United States Patent [19]

Schultz et al.

[11] Patent Number: 5,514,953
[45] Date of Patent: May 7, 1996

[54] WAFER LEVEL TEST STRUCTURE FOR DETECTING MULTIPLE DOMAINS AND MAGNETIC INSTABILITY IN A PERMANENT MAGNET STABILIZED MR HEAD

[75] Inventors: Allan E. Schultz, St. Paul; Peter K. George, Bloomington; William P. Wood, Edina; Duane C. Phinney; Patrick J. Ryan, both of St. Paul, all of Minn.

[73] Assignee: Seagate Technology, Inc., Scotts Valley, Calif.

[21] Appl. No.: 437,692

[22] Filed: May 9, 1995

Related U.S. Application Data

[63] Continuation-in-part of Ser. No. 201,666, Feb. 24, 1994, abandoned.

[51] Int. Cl.[6] .......................... G01R 33/12; G01N 27/82; H01L 43/08; G11B 5/39
[52] U.S. Cl. .............. 324/228; 29/593; 324/235; 324/252; 324/537
[58] Field of Search ..................... 324/202, 228, 324/234, 235, 238, 252, 537, 693, 702, 705, 706, 719; 338/32 R; 360/113; 29/593, 595, 603, 610.1

[56] References Cited

U.S. PATENT DOCUMENTS 5,247,276  9/1993  Pant et al. .................... 338/32 R
5,260,653  11/1993  Smith et al. .................. 324/252

*Primary Examiner*—Gerard R. Strecker
*Attorney, Agent, or Firm*—Kinney & Lange

[57] ABSTRACT

A wafer level test structure and method detects multiple magnetic domains and magnetic domain instability in a test magnetic element. The apparatus comprises a first MR sensor designed to be held in a single magnetic domain by shape anisotropy and a second MR sensor having a permanent magnet to hold the element in a single magnetic domain. A circuit connects the first and second MR sensors to detect differences between the changes in resistance between the first and second sensors in the presence of a magnetic field or differences in resistance after the application and release of a magnetic field. The circuit is preferably a balance circuit in which imbalance in the presence of a magnetic field indicates the presence of multiple magnetic domains in at least one of the test sensors. Magnetic domain stability may be tested by applying an external field to disrupt the existing single domain state of the test sensors, and thereafter detecting differences in resistance of the sensors during reversal of the magnetic field.

27 Claims, 4 Drawing Sheets

WAFER LEVEL TEST STRUCTURE FOR DETECTING MULTIPLE DOMAINS AND MAGNETIC INSTABILITY IN A PERMANENT MAGNET STABILIZED MR HEAD

CROSS REFERENCE TO RELATED APPLICATIONS

This application is a continuation-in-part of application Ser. No. 08/201,666 filed Feb. 24, 1994, now abandoned.

BACKGROUND OF THE INVENTION

This invention relates to production of magnetic elements, and particularly to the formation of magnetoresistive elements for use in a transducing head or the like. More particularly, the invention relates to detection of multiple magnetic domains and of the stability of magnetic domains in magnetic elements being formed on a wafer.

Magnetoresistive (MR) sensors are responsive to changes in magnetic fields by changing resistance. Such sensors are increasingly employed as read transducers in the heads of magnetic disc drives, primarily because the change of resistance in the sensor is independent of disc speed and depends primarily upon changes in the magnetic flux. These sensors typically comprise a thin strip of NiFe alloy (Permalloy) of low coercivity, with an easy axis of magnetization along the strip. Many other ferromagnetic materials are also candidates, although Permalloy is the most commonly used. Recently, the strips have been mounted on the head between permanent magnet wings to stabilize the head to a single magnetic domain. Additionally, soft magnetic layers (SALs) have been placed adjacent the strips to further stabilize the head.

One problem encountered with MR sensors is Barkhausen noise caused by the irreversible motion of magnetic domains in the presence of an applied field. It is known that Barkhausen noise is eliminated by creation of a single magnetic domain in the sense current region of the MR element. However, multiple magnetic domains may be formed during fabrication of the MR element. It is, therefore, important to be able to identity, MR elements having multiple magnetic domains.

The patterning of permanent magnets on a wafer involves ion milling into or through the Permalloy, deposition and lift-off of the permanent magnet film, and patterning of the Permalloy and permanent magnet films that form the sensor structure. Finally, the active area is defined by the contacts. Substantial processing problems in any one of these steps, or a combination of minor problems in more than one of these steps, can cause the formation of a multiple domain sensor. For example, pinning sites at the contact edges or insufficient stabilizing field on the permanent magnets can lead to multiple domain sensors. More particularly, the stabilizing effect of the permanent magnet wings of a permanent magnet stabilized MR head is considered to be sensitive to process parameters. An inadequately stabilized film could, for example, be formed by too thin of a permanent magnet film or the placement of permanent magnets too far from the sensor, or formation of an active region having too high or too low of a height to achieve reliable repeatability. The performance of the head could also be affected in other ways related to the presence of a multiple-domain sensor. It is, therefore, important to be able to identify MR elements having multiple magnetic domains or which destabilize in an external magnetic field.

Previously, MR elements had been sorted through inspection in a Kerr effect microscope by visually determining when the domains changed under rotation of the magnetic field. MR elements have also been sorted by examining the elements using magnetic force microscopy. Both inspection methods require expensive equipment not normally used in production, and both are labor intensive and tedious. Furthermore, these processes are expensive and time consuming, and the use of the Kerr effect microscope is also inaccurate for very small elements. Transfer curve testing, which is quick and inexpensive, has been used to detect Barkhausen noise, but transfer curve testing requires saturation of magnetic shields adjacent the element to avoid generation of inaccurate data.

SUMMARY OF THE INVENTION

The present invention provides an apparatus and method for detecting multiple magnetic domains and single magnetic domain instability in a test magnetic element. The apparatus comprises a first MR element designed to be held in a single magnetic domain by shape anisotropy and a second MR element having a permanent magnet to hold the element in a single magnetic domain. A circuit connects the first and second MR elements to detect differences between the changes in resistance between the first and second elements in the presence of a magnetic field or differences in resistance after the application of a magnetic field.

One feature of the present invention resides in the provision of the apparatus as part of a wafer level test structure on the wafer on which the magnetoresistive elements are being formed. According to one form of the invention the circuit is a Wheatstone bridge that becomes unbalanced due to differences between the change of resistance between the first and second elements.

One form of the present invention employs a plurality of wafer level test structures on the wafer to map unstable single magnetic domain state or multiple magnetic domain state in the magnetoresistive material as an indication of the condition of permanent magnet stabilized magnetoresistive transducers being constructed.

In one form of the invention, the second MR of each test structure has geometric parameters defined by the height and width of the respective magnetoresistive element and the separation between the pair of contacts of the sensor. The geometric parameters of the test structures on the wafer vary from one test structure to another. Measurements of the various test structures are mapped by comparing measurements based on geometric parameters, thus providing a measure of optimal fabrication processes.

According to the process of the present invention, a saturation field is applied along the long axis of the sensor (X direction) and the circuit is balanced. The external magnetic field is then released, either in one or several stages, and any imbalance in the circuit is measured. Imbalance of the circuit in the presence of a magnetic field indicates the presence of multiple magnetic domains in at least one of the test elements. An external field may also be applied to the test elements to disrupt an existing single domain state to test the stability of the element. Since the fabrication and geometry of the permanent magnet test structure are identical to those of the devices in production on the wafer, the presence of magnetic domain instability or multiple magnetic domains in the test elements is an indicator that the permanent magnet stabilized MR elements on the entire wafer also have magnetic domain instability or multiple magnetic domains.

DETAILED DESCRIPTION OF THE PREFERRED EMBODIMENTS

Figure 1:
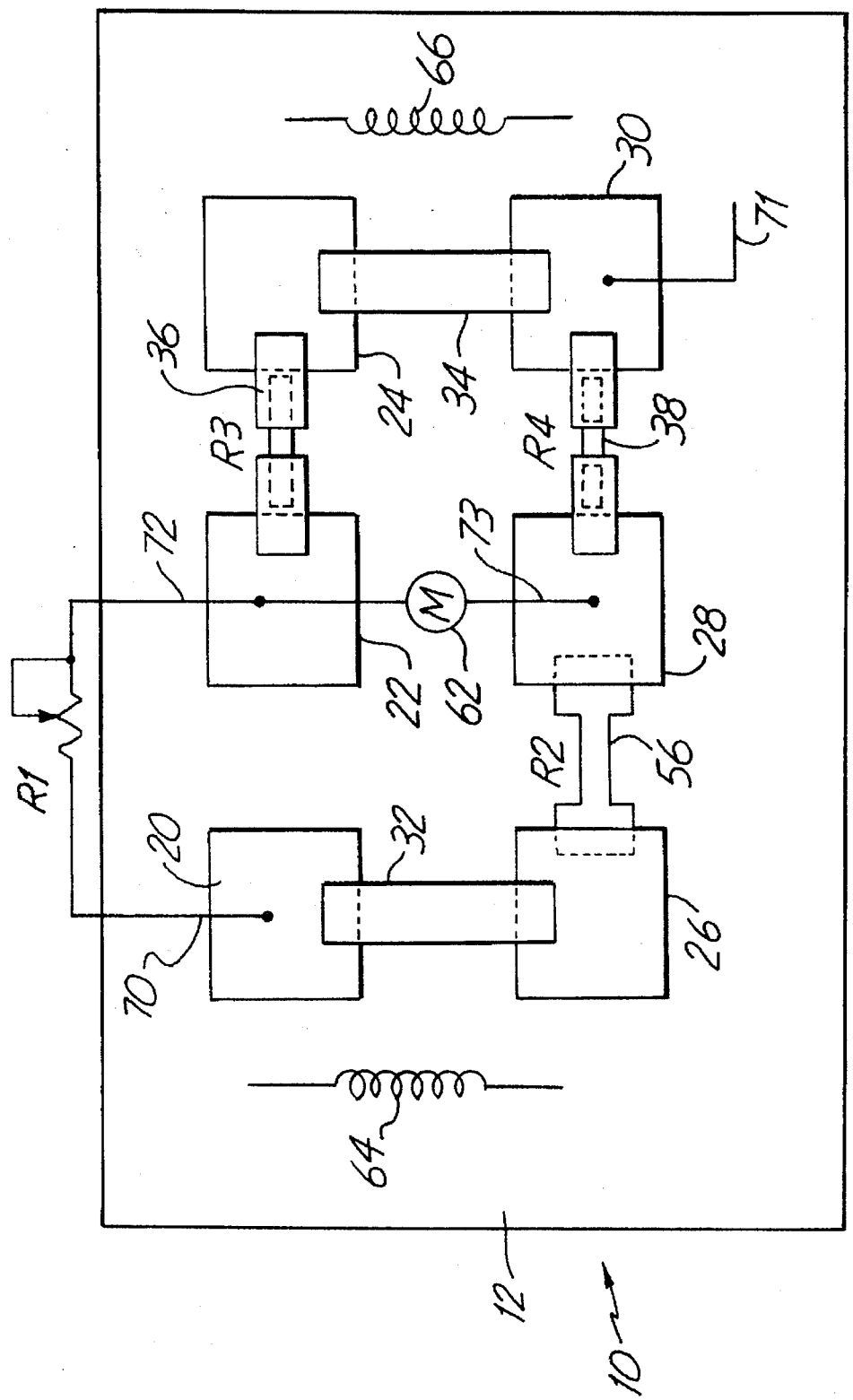
FIG. 1 is a plan view of a wafer level test structure in accordance with the presently preferred embodiment of the present invention.

FIG. 1 illustrates a test structure 10 which may be part of a wafer on which magnetoresistive (MR) elements are fabricated. More particularly, test structure 10 may be formed on wafer substrate 12. Test structure 10 includes a plurality of non-magnetic, conductive film pads 20, 22, 24, 26, 28 and 30. Non-magnetic metallization contacts 32 and 34 function as bus bars to directly connect pads 20 and 26 and 24 and 30, respectively. In the preferred embodiment of the present invention, the test structure is formed of ordinary wafer pads having the same configuration as the wafer pads used in production of MR elements. The six wafer pads could be reduced to four by combining pads 24 and 30 and pads 20 and 26 to accommodate the four points of a Wheatstone bridge. The use of six pads permits use of the same pad layout for all test structures, some of which require six pads.

Figure 2A:
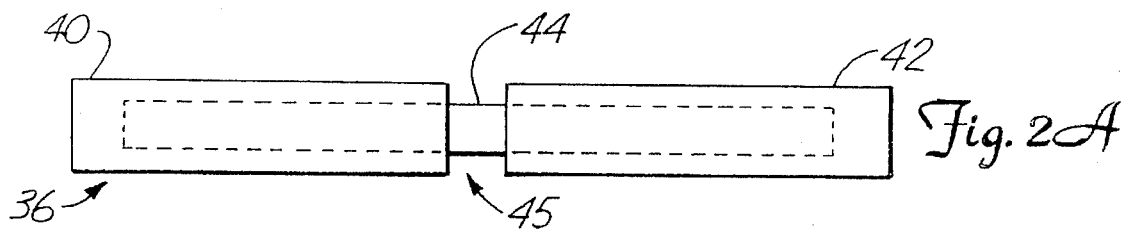
FIGS. 2A and 2B are plan views of a first magnetoresistive element held in a single magnetic domain by shape anisotropy and a second magnetoresistive sensor held in a single magnetic domain by permanent magnets.

A first MR sensor 36 is formed between pads 22 and 24 and a second MR sensor 38 is formed between pads 28 and 30. Sensors 36 and 38 are shown in greater detail in FIGS. 2A and 2B. More particularly, sensor 36 comprises a long strip 44 of Permalloy deposited on substrate 12. The substrate may be an insulating layer of oxide or other suitable material, or it may include a magnetic shield material, such as Sendust or Permalloy under an insulator layer. First and second metal contacts 40 and 42 are deposited on strip 44, substrate 12 and contacting pads 22 and 24, respectively. Permalloy strip 44 bridges the space between metal contacts 40 and 42 and is held in a single domain state by its shape anisotropy. More particularly, the contacts are patterned to define an active area 45 of sensor 36 capable of producing an MR response. Hence, strip 44 and contacts 40 and 42 form a first magnetoresistive sensor which bridges between pads 22 and 24 in FIG. 1.

Figure 2B:
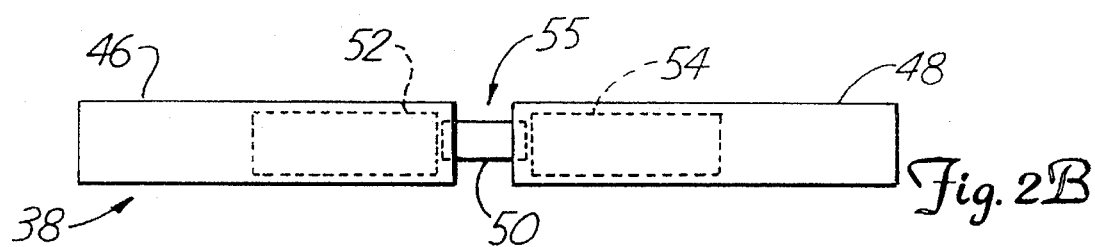

As shown particularly in FIG. 2B, sensor 38 comprises a much shorter rectangular strip 50 of Permalloy identical to the Permalloy forming strip 44. Permalloy strip 50 has a geometry where shape anisotropy stabilization is minimal. Permanent magnets 52 and 54 are deposited on or adjacent to element 50 to hold element 50 to a single domain state. For example, magnets 52 and 54 may be deposited directly onto substrate 12, or on a small residual film of element 50, or butted up directly adjacent to element 50. Contacts 46 and 48 are patterned to define active area 55 of sensor 38. The active areas 45 and 55 are sized identically. Metal contacts 46 and 48 provide connections of sensor 38 to pads 28 and 30, respectively. Also, as shown particularly in FIG. 1, sensors 36 and 38 form resistors R3 and R4 to the sensor circuit, shown in FIG. 3.

Although sensors 36 and 38 are illustrated with having contact edges that are perpendicular to the easy axis, the edges may be slanted, like those in a barber-pole design.

As shown in FIG. 1, a resistor 56 is formed between pads 26 and 28. Resistor 56 is formed of non-magnetic material and has dimensions chosen to provide a resistance value that is nearly equal to those of one or the other of sensors 36 and 38, to facilitate the initial balance to the sensing circuit. Resistor 56 forms resistor R2 of the circuit of FIG. 3.

The two magnetoresistive sensors 36 and 38 have identically sized active areas, but one is a permanent magnet stabilized sensor and the other is a sensor whose single domain state is stabilized by shape anisotropy. Sensors 36 and 38 are formed at the same time, during the same deposition processes, and using the same materials as other MR elements on the wafer, and, were they used for heads, would produce an unbiased MR response. More particularly, the MR elements being fabricated and the test structure 10 are formed on a wafer by depositing and patterning the MR (Permalloy) material (including elements 44, 50 and 56), ion milling the MR elements, depositing the permanent magnet films 52 and 54, patterning the permanent magnets by liftoff; and depositing and patterning the contacts (including contacts 32, 34, 40, 42, 46 and 48). The MR elements being fabricated may be of the type held in a single magnetic domain by permanent magnets or by shape anisotropy. An example of a permanent magnet stabilized MR head is described in U.S. patent application Ser. No. 07/936,185 filed Aug. 25, 1992 for "Improved Read Sensitivity MR Head Using Permanent Magnetic Longitudinal Stability" by P. K. George and G. A. Garrettson and assigned to the same assignee as the present invention, and examples of shape anisotropy stabilized MR heads are described in U.S. Pat. No. 4,967,298 for "Magnetic I Head with Magnetoresistive Sensor, Inductive Write Head, and Shield" and in U.S. Pat. No. 5,208,715 for "Shield Geometry for Stabilizing Magnetic Domain Structure in a Magnetoresistive Head", both by G. S. Mowry and assigned to the same assignee as the present invention; the George et al. application and Mowry patents are incorporated herein by reference. In applications of the present invention to production of SAL (soft adjacent layer) MR heads, sensor 38 may additionally incorporate an SAL formed of ferromagnetic material such as nickel-iron-rhodium, nickel-iron-rhenium, or nickel-iron-chromium, as described in U.S. patent application Ser. No. 08/380,820 filed Jan. 30, 1995 for "Magnetoresistive Sensor with Improved Performance and Processability" by Peter I. Bonyhard, James F. Dolejsi, Charles H. Tolman and William P. Wood and assigned to the same assignee as the present invention.

In use, a variable resistor R1 is attached, such as by probes, between pads 20 and 22 to form a balancing resistance to the test circuit. An appropriate power supply 60 (FIG. 3) is attached to pads 20 and 30, and a suitable voltmeter 62 is attached to pads 22 and 28. Typically, these connections may be made by a single probe assembly comprising a card having probe pins 70, 71.72 and 73. Preferably, the probe assembly should also be equipped with field coils 64, 66 capable of generating magnetic fields of adequate strength to saturate the sensors 36 and 38, along with any shields if present. If the probe assembly does not itself contain field coils, an external magnetic field source is necessary. A magnetic field of about 100 Oe is adequate for most cases.

Figure 3:
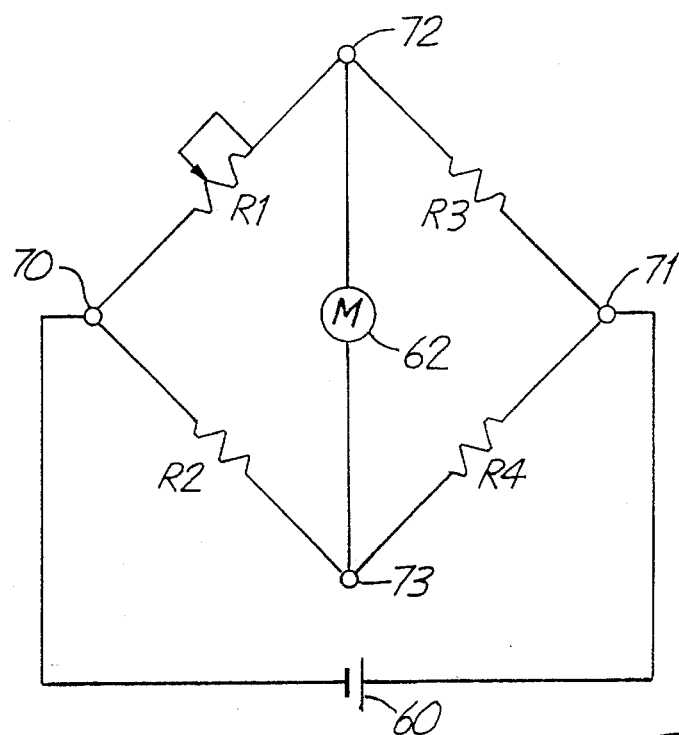
FIG. 3 is a circuit diagram of the test structure of FIG. 1.
Figure 4A:
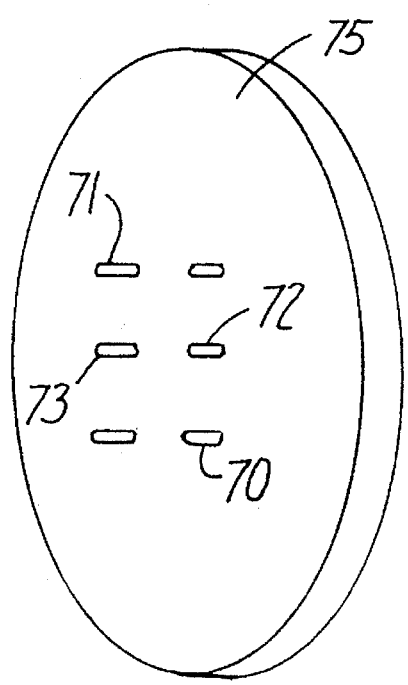
FIGS. 4A and 4B illustrate a typical probe card used in the testing of wafers according to the present invention.
Figure 4B:
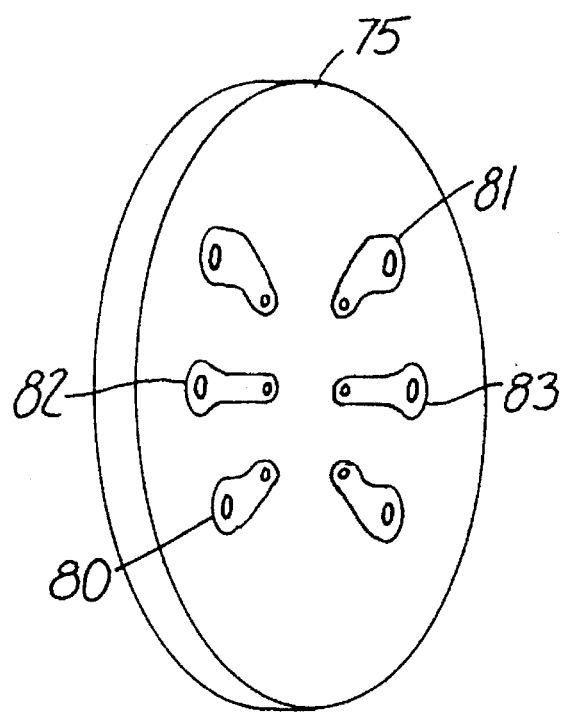

FIGS. 4A and 4B illustrate opposite sides of a typical probe card used in the test. One example probe card is Model No. E701X8.375 available from Alphatronics Engineering Corporation of Colorado Springs, Colo. The probe card includes six pins mounted to one side of wafer 75 (FIG. 4A) arranged to engage pads 20, 22, 24, 26, 28 and 30 on substrate 12. The six pins include pins 70, 71, 72 and 73, diagrammatically illustrated in FIG. 1, to engage pads 20, 30, 22 and 28, respectively. The opposite side of wafer 75 (FIG. 4B) includes circuit traces connected to respective pins and terminating at terminals for connection to external equipment. Terminal 80 is connected to pin 70, terminal 81 is connected to pin 71, terminal 82 is connected to pin 72 and terminal 83 is connected to pin 73. Power source 60 (FIG. 3) is connected through terminals 80 and 81 and pins 70 and 71 to pads 20 and 30, resistor R1 is connected through terminals 80 and 82 and pins 70 and 72 to pads 20 and 22, and meter 62 is connected through terminals 82 and 83 and pins 72 and 73 to pads 22 and 28, all as illustrated in FIGS 1 and 3.

Initially, a magnetic field (such as between about +50 and +100 Oe) is applied to the sensors so that the sensors assume a single domain state. Any small differences in resistance between sensors 36 and 38 are balanced by adjusting resistor R1. The magnetic field applied to sensors 36 and 38 by field coils 64 and 66 is slowly reduced and reversed (to about −20 Oe). The shape anisotropy stabilized sensor 36 should remain single domain during the procedure. However, if the permanent magnet stabilization is inadequate, the associated MR active area of sensor 38 will become multi-domain. In a multi-domain sensor (such as the now unstablized sensor 38), the presence of closure domains reduces the effective active area for the sensors to produce an MR response. The effect will likely be greater on sensor 38 than sensor 36 because sensor 36 is at least partially held to single magnetic domains by the long MR structure, whereas defects in the permanent magnet stabilizing films of sensor 38 are more likely to allow sensor 38 to develop multiple magnetic domains. Consequently, if closure domains are present, a small resistance difference will arise between sensors 36 and 38 while the magnetic field is reduced and reversed to the sensors. The amount of imbalance of the bridge circuit is indicative of the resistance difference due solely to differences in magnetoresistive response between sensors 36 and 38. Variable resistor R1 is then adjusted to restore balance to the circuit while, at the same time, measuring the resistance change required to reach balance. Because both MR sensors 36 and 38 are part of the bridge circuit, the resistance change can be measured to great precision and provides a measurement of the extent of multiple magnetic domains in the MR elements.

As a separate test, even if a single domain state exists in the sensors, external magnetic fields can be applied by coils 64 and 66 to disrupt the single domain state so that, upon removal of the field, any balancing required of the Wheatstone bridge circuit is a measurement of the sensor's stability, or lack thereof.

Figure 5A:
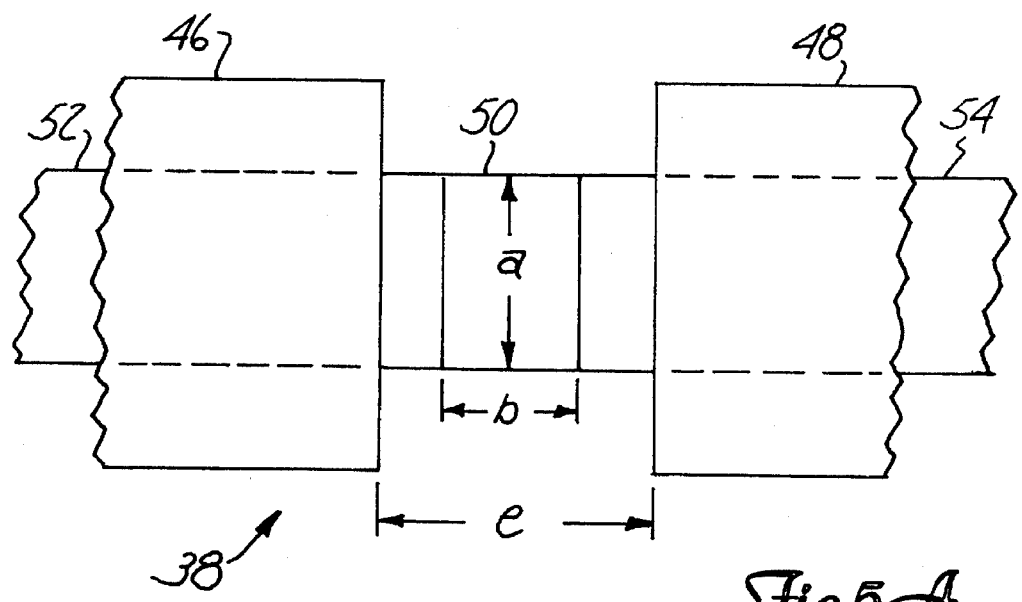
FIGS. 5A and 5B illustrate configurations of the second magnetoresistive sensor for optimizing the test process.
Figure 5B:
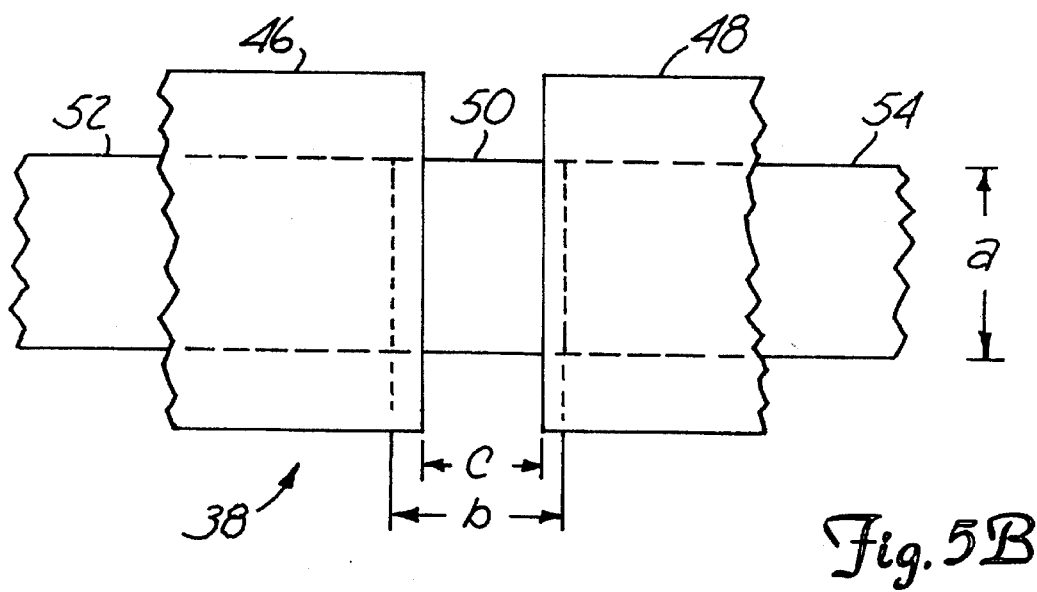

FIGS. 5A and 5B illustrate various geometries of sensor 38. As shown in FIG. 5A, permanent magnets 52 and 54 are positioned adjacent Permalloy strip 50 with metal contacts 46 and 48 over and in contact with the permanent magnets outside the bounds between the magnets and strip 50. FIG. 5B shows sensor 38 with its contacts 46 and 48 extending over the bounds into direct contact with Permalloy strip 50. In each case, sensor 38 has dimensions a, b, and c that define the height (a) of the magnetoresistive sensing element, the width (b) of the magnetoresistive strip along the easy axis, and the distance (c) between contacts 46 and 48 along the easy axis. The active area, therefore, is defined by the smaller dimension of b and c. For best results, the active area of sensor 38 for a given test structure should equal the active area of sensor 36 for the same test structure, but it is not necessary that the active areas of the sensors of all test structures on a wafer be equal. Additionally, as described above, sensor 38 may be constructed with a soft adjacent layer (SAL) of soft magnetic material adjacent strip 50, such as when the test structure is employed on wafers where SALs are formed adjacent the magnetoresistive materials of the head structures being formed on the wafer.

A plurality of test structures 10 may be positioned at various locations on a wafer. By applying the probe card shown in FIG. 4 to each of the test structures on the wafer, tests can be performed in a short period of time at a variety of locations on the wafer to map detective or unstable MR elements on the wafer.

By employing test structures 10 having different geometries of dimensions a, b, c for sensor 38, the effectiveness of the manufacturing process for permanent magnet stabilized transducers may be mapped by charting the position of effective and stable test structure sensors on the wafer in accordance with the various geometric parameters. Hence, not only can defective and unstable elements be mapped, but the test structure may be employed to determine the effectiveness of the manufacturing process. Moreover, comparison of test results between several wafers may be used to determine repeatability of the manufacturing process over several wafers and to define optimal geometric parameters for the dimensions a, b, and c.

Thus, the test structure provides a mechanism for determining the effectiveness of the manufacturing process as well as optimizing the geometry of the heads being produced by the manufacturing process for purposes of high reliability and repeatability of the parameters of that head. Hence, it is possible to achieve heads from various wafers having consistently similar parameter, thereby reducing the amount of calibration required during assembly of the heads into disc drives.

Although the present invention has been described with reference to preferred embodiments, workers skilled in the art will recognize that changes may be made in form and detail without departing from the spirit and scope of the invention.

What is claimed is:

1. A wafer level test structure for indicating an unstable single magnetic domain state or multiple magnetic domain state in a magnetoresistive material fabricated on the wafe,r the test structure comprising:

a first magnetoresistive sensor formed in the magnetoresistive material on the wafer and arranged to be held in a single magnetic domain state by shape anisotropy;

a second magnetoresistive sensor formed in the magnetoresistive material on the wafer and arranged to be held in a single magnetic domain state by permanent magnet;

means for applying a variable magnetic field to the first and second magnetoresistive sensors; and a circuit connected to the first and second magnetoresistive sensors to detect a difference between a resistance of the first magnetoresistive sensor and a resistance of the second magnetoresistive sensor and to detect a change in the difference between the resistances of the first and second magnetoresistive sensors upon a change in the applied magnetic field.

2. The wafer level test structure of claim 1, wherein the circuit is a balanced circuit, the circuit including a variable resistor for balancing resistances of the first and second magnetoresistive sensors and an indicator for indicating the balanced condition of the circuit.

3. The wafer level test structure of claim 2, wherein the circuit is a Wheatstone bridge.

4. The wafer level test structure of claim 1, including a fixed resistor on the wafer connected to at least one of the first and second sensors.

5. The wafer level test structure of claim 1, wherein the circuit includes a probe card containing a power source, a power indicator and a variable resistor, a first probe connected to a first side of the power source and a first side of the variable resistor a second probe connected to a second side of the variable resistor and a first side of the indicator, a third probe connected to a second side of the power source and a fourth probe connected to a second side of the indicator, the first probe being arranged to be connected to a first side of the fixed resistor, the second probe being arranged to be connected to a first side of one of the sensors, the third probe being arranged to be connected between the first and second sensors, and the fourth probe being arranged to be connected between the second side of the fixed resistor and the opposite side of the other of the sensors.

6. The wafer level test structure of claim 5, wherein the means for applying a variable magnetic field includes field coils for applying a magnetic field to the first and second sensors.

7. In a wafer having a magnetoresistive material from which plural permanent magnet stabilized magnetoresistive transducers are to be constructed, the improvement comprising:

a plurality of wafer level test structures for indicating an unstable single magnetic domain state or multiple magnetic domain state in the magnetoresistive material, each test structure comprising:

a first magnetoresistive sensor formed in the magnetoresistive material on the wafer and arranged to be held in a single magnetic domain state by shape anisotropy; and a second magnetoresistive sensor formed in the magnetoresistive material on the wafer and arranged to be held in a single magnetic domain state by permanent magnet;

means for applying a variable magnetic field to the first and second magnetoresistive sensors of at least a selected test structure; and a circuit disposed and arranged to be connected to the first and second magnetoresistive sensors of at least one selected test structure to detect a difference between a resistance of the first magnetoresistive sensor and a resistance of the second magnetoresistive sensor of the selected test structure and to detect a change in the difference between the resistances of the first and second magnetoresistive sensors of the selected test structure upon a change in the applied magnetic field.

8. The apparatus of claim 7, wherein the circuit is a balanced circuit, the circuit including a variable resistor for balancing resistances of the first and second magnetoresistive sensors of the selected test structure and an indicator for indicating the balanced condition of the circuit.

9. The apparatus of claim 8, wherein the circuit is a Wheatstone bridge.

10. The apparatus of claim 7, wherein each test structure includes a fixed resistor on the wafer connected to at least one of the respective first and second sensors.

11. The apparatus of claim 7, wherein the circuit includes a probe card containing a power source, a power indicator and a variable resistor, a first probe connected to a first side of the power source and a first side of the variable resistor, a second probe connected to a second side of the variable resistor and a first side of the indicator, a third probe connected to a second side of the power source and a fourth probe connected to a second side of the indicator, the first probe being arranged to be connected to a first side of the fixed resistor of a selected test structure, the second probe being arranged to be connected to a first side of one of the sensors of the selected test structure, the third probe being arranged to be connected between the first and second sensors of the selected test structure, and the fourth probe being arranged to be connected between the second side of the fixed resistor and the opposite side of the other of the sensors of the selected test structure.

12. The apparatus of claim 11, wherein the means for applying a variable magnetic field includes field coils mounted to the probe card for applying a magnetic field to the first and second sensors of the selected test structure.

13. The apparatus of claim 7, wherein the second magnetoresistive sensor of each test structure comprises a pair of permanent magnets on the wafer, a pair of contacts adjacent at least the permanent magnets, and a magnetoresistive element formed in the magnetoresistive material between ones of the pair of permanent magnets, the pair of permanent magnets being arranged to hold the magnetoresistive element in a single magnetic domain state, the magnetoresistive element having an active region defined by the pair of permanent magnets or pair of contacts, the second magnetoresistive sensor of each test structure having geometric parameters defined by a height and a width of the respective magnetoresistive element and the distance of separation between the pair of contacts, the geometric parameters of at least one test structure on the wafer being different from the geometric parameters of at least another test structure on the wafer.

14. A process for testing magnetic domains in a magnetoresistive material on a wafer, the process comprising:

providing a test structure on the wafer having a first magnetoresistive sensor designed to be held in a single magnetic domain state by shape anisotropy, a second magnetoresistive sensor and a permanent magnet designed to stabilize the second magnetoresistive sensor in a single magnetic domain state, the first and second magnetoresistive sensors being formed in the magnetoresistive material;

applying a magnetic field to the first and second magnetoresistive sensors;

changing the applied magnetic field; and detecting a change in a difference between a resistance of the first magnetoresistive sensor and a resistance of the second magnetoresistive sensor upon a change in the applied magnetic field.

15. The process of claim 14, further including measuring the changes in difference of resistance.

16. The process of claim 15, further including a balance circuit and the changes in difference of resistance is measured by balancing the circuit.

17. The process of claim 14, wherein the magnetic field is applied to the magnetoresistive sensors in one direction to at a strength to disrupt any single magnetic domain state in the magnetoresistive sensors, and further including reducing the strength of the magnetic field in the one direction while detecting a change in difference between the resistances of the first and second magnetoresistive sensors.

18. The process of claim 17, wherein the test structure includes a balance circuit, and the change in difference in resistance is measured by balancing the circuit.

19. The process of claim 17, including reversing the direction of the magnetic field.

20. The process of claim 14, wherein the magnetic field is applied to the first and second magnetoresistive sensors in a first direction at a strength so that the first and second magnetoresistive sensors assume single magnetic domain states, the process further including reversing the magnetic field to a second direction opposite the first direction while detecting a change in difference between the resistances of the first and second magnetoresistive sensors.

21. The process of claim 14, wherein a plurality of permanent magnet stabilized magnetoresistive transducers are to be constructed on the wafer, the process including providing a plurality of test structures on the wafer, measuring a change in a difference between a resistance of the first magnetoresistive sensor of each test structure and a resistance of the second magnetoresistive sensor of the respective test structure upon a change in the applied magnetic field, and mapping the measurements as an indication of the magnetic domain stability or presence of multiple magnetic domain states of the transducers being constructed.

22. The process of claim 21, wherein the second magnetoresistive sensor of each test structure comprises a pair of permanent magnets on the wafer, a pair of contacts adjacent at least the permanent magnets, and a magnetoresistive element formed in the magnetoresistive material between ones of the pair of permanent magnets and has geometric parameters defined by a height and a width of the respective magnetoresistive element and the distance of separation between the pair of contacts, the geometric parameters of at least one test structure on the wafer being different from the geometric parameters of at least another test structure on the wafer, the step of mapping measurements includes comparing measurements derived from test structures based on geometric parameters.

23. A process for indicating unstable single magnetic domain states or multiple magnetic domain states in a magnetoresistive material on a wafer, comprising:

forming a test structure on the wafer, the test structure comprising a first magnetoresistive sensor arranged to a single magnetic domain state by shape anisotropy and a second magnetoresistive sensor arranged to a single magnetic domain state by permanent magnet, the first and second magnetoresistive sensors being formed in the magnetoresistive material;

applying a magnetic field to the first and second magnetoresistive sensors so that the sensors each assume single magnetic domain states;

changing the applied magnetic field; and detecting change in a difference between resistances of the first and second magnetoresistive sensors upon the change in the applied magnetic field.

24. The process of claim 23 wherein the applied magnetic field is changed by reversing the direction of the magnetic field, and the change in the difference between the resistances of the first and second magnetoresistive sensors is indicative of the presence of multiple domain states in the second magnetoresistive sensor.

25. The process of claim 23 wherein the applied magnetic field is changed by removing the magnetic field from the sensors, and the change in the difference between the resistances of the first and second magnetoresistive sensors is indicative of the presence of an unstable single magnetic domain state in a magnetoresistive sensor.

26. The process of claim 23, wherein a plurality of permanent magnet stabilized magnetoresistive transducers are to be constructed on the wafer, the process including providing a plurality of test structures on the wafer, measuring a change in a difference between a resistance of the first magnetoresistive sensor of each test structure and a resistance of the second magnetoresistive sensor of the respective test structure upon a change in the applied magnetic field, and mapping the measurements as an indication of the magnetic domain stability or presence of multiple magnetic domain states of the transducers being constructed.

27. The process of claim 26, wherein the second magnetoresistive sensor of each test structure comprises a pair of permanent magnets on the wafer, a pair of contacts adjacent at least the permanent magnets, and a magnetoresistive element formed in the magnetoresistive material between ones of the pair of permanent magnets, and has geometric parameters defined by a height and a width of the respective magnetoresistive element and the distance of separation between the pair of contacts, the geometric parameters of at least one test structure on the wafer being different from the geometric parameters of at least another test structure on the wafer, the step of mapping measurements includes comparing measurements derived from test structures based on geometric parameters.

\* \* \* \* \*

UNITED STATES PATENT AND TRADEMARK OFFICE
CERTIFICATE OF CORRECTION

PATENT NO. : 5,514,953
DATED : May 7, 1996
INVENTOR(S) : Allan E. Schultz, et al It is certified that error appears in the above-indentified patent and that said Letters Patent is hereby corrected as shown below:

Col. 1, line 43, delete "identity", insert --identify--

Col. 4, line 22, after "liftoff", delete ";", insert --,--

Col. 4, line 34, after "Magnetic", delete "I"

Col. 4, line 57, after "71", delete ".", insert --,--

Col. 6, line 14, delete "detective", insert --defective--

Col. 6, line 46, delete "wafe,r", insert --wafer,--

Col. 8, line 27, delete "clement", insert --element--

Signed and Sealed this

Twenty-third Day of July, 1996

Attest:

BRUCE LEHMAN

*Attesting Officer*     *Commissioner of Patents and Trademarks*